US00PP15321P2

(12) United States Plant Patent
Westhoff

(10) Patent No.: US PP15,321 P2
(45) Date of Patent: Nov. 16, 2004

(54) ***PETUNIA* PLANT NAMED 'WESPEQUEEN'**

(50) Latin Name: *Petunia×hybrida*
Varietal Denomination: Wespequeen

(75) Inventor: Heinrich Westhoff, Südlohn (DE)

(73) Assignee: Josef & Heinrich Westhoff Gartenbau-Spezialkulturen, Südlohn-Oeding (DE)

( * ) Notice: Subject to any disclaimer, the term of this patent is extended or adjusted under 35 U.S.C. 154(b) by 0 days.

(21) Appl. No.: 10/759,721

(22) Filed: Jan. 16, 2004

(51) Int. Cl.[7] ..... A01H 5/00
(52) U.S. Cl. ..... Plt./356
(58) Field of Search ..... Plt./356

*Primary Examiner*—Anne Marie Grunberg
*Assistant Examiner*—Annette H Para
(74) *Attorney, Agent, or Firm*—C. A. Whealy

(57) ABSTRACT

A distinct cultivar of *Petunia* plant named 'Wespequeen', characterized by its cascading growth habit; freely flowering habit; single bicolored flowers that are purple in color with white-colored margins; light bluish violet-colored anthers; and large sepals.

1 Drawing Sheet

Botanical classification/cultivar designation: *Petunia×hybrida* cultivar Wespequeen.

BACKGROUND OF THE INVENTION

The present Invention relates to a new and distinct cultivar of *Petunia* plant, botanically known as *Petunia×hybrida*, and hereinafter referred to by the name 'Wespequeen'.

The new *Petunia* is a product of a planned breeding program conducted by the Inventor in Südlohn-Oeding, Germany. The new *Petunia* originated from a cross-pollination made by the Inventor of a proprietary *Petunia* seedling selection, not patented, as the female, or seed parent, identified as code number 99P078 with a proprietary *Petunia* seedling selection not patented, as the male, or pollen, parent, identified as code number 99P048. The new *Petunia* was selected by the Inventor in 2000 in a controlled environment in Südlohn-Oeding, Germany.

Asexual reproduction of the new cultivar by terminal cuttings in Südlohn-Oeding, Germany since 2001, has shown that the unique features of this new *Petunia* are stable and reproduced true to type in successive generations.

SUMMARY OF THE INVENTION

Plants of the cultivar 'Wespequeen' have not been observed under all possible environmental conditions. The phenotype may vary somewhat with variations in environment such as temperature, daylength, and light intensity without, however, any variance in genotype.

The following traits have been repeatedly observed and are determined to be the unique characteristics of 'Wespequeen'. These characteristics in combination distinguish 'Wespequeen' as a new and distinct *Petunia* cultivar:

1. Cascading growth habit.
2. Freely flowering habit.
3. Single bicolored flowers that are purple in color with white-colored margins.
4. Light bluish violet-colored anthers.
5. Large sepals.

Plants of the new *Petunia* produce flowers that are larger and darker in color than plants of the female parent, a proprietary selection. Plants of the new *Petunia* have a more cascading plant habit and have larger and darker colored flowers than plants of the male parent, a proprietary selection.

Plants of the cultivar Wespequeen can be compared to plants of the *Petunia* cultivar Brevt, described in U.S. Plant Pat. No. 12,679. However in side-by-side comparisons conducted in Südlohn-Oeding, Germany, plants of the new *Petunia* and the cultivar Brevt, differed in the following characteristics:

1. Plants of the new *Petunia* had shorter internodes than plants of the cultivar Brevt.
2. Plants of the new *Petunia* had larger flowers with larger sepals than plants of the cultivar Brevt.
3. Flower color of plants of the new *Petunia* was different than flower color of plants of the cultivar Brevt.
4. Plants of the new *Petunia* had longer peduncles than plants of the cultivar Brevt.
5. Flowers of the new *Petunia* had anthers of a different color than flowers of the cultivar Brevt.

Plants of the cultivar 'Wespequeen' can also be compared to plants of the *Petunia* cultivar Bresh, disclosed in U.S. Plant patent application Ser. No. 09/592,379, now abandoned. However in side-by-side comparisons conducted in Südlohn-Oeding, Germany, plants of the new *Petunia* and the cultivar Bresh differed in the following characteristics:

1. Plants of the new *Petunia* had shorter internodes than plants of the cultivar Bresh.
2. Plants of the new *Petunia* had larger flowers with larger sepals than plants of the cultivar Bresh.
3. Flower color of plants of the new *Petunia* was more intense than flower color of plants of the cultivar Bresh.
4. Flowers of the new *Petunia* had anthers of a different color than flowers of the cultivar Bresh.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description, which accurately describe the colors of the new *Petunia*.

The photograph comprises a side perspective view of a typical plant of 'Wespequeen'.

DETAILED BOTANICAL DESCRIPTION

In the following description, color references are made to The Royal Horticultural Society Colour Chart, 2001 Edition, except where general terms of ordinary dictionary significance are used. Plants used for the aformentioned photographs and the following botanical description were grown in 12-cm containers during the spring and summer for about 20 weeks in a glass-covered greenhouse and under conditions that closely approximate commercial production conditions in Südlohn-Oeding, Germany. During the production of the plants, day temperatures were about 20 to 25° C., night temperatures were about 16 to 18° C. and light levels ranged from 3,000 to 50,000 lux.

Botanical classification: *Petunia×hybrida* cultivar Wespequeen.

Parentage:

*Female parent.*—Proprietary *Petunia×hybrida* selection identified as code number 99P078, not patented.

*Male parent.*—Proprietary *Petunia×hybrida* selection identified as code number 99P048, not patented.

Propagation:

*Type cutting.*—Terminal vegetative cuttings.

*Time to initiate roots.*—About 18 days at 20° C.

*Time to develop roots.*—About 20 to 28 days at 20° C.

*Root description.*—Numerous, fine, fibrous and well-branched.

Plant description:

*Form.*—Annual flowering plant; cascading plant habit. Viscid, glandular pubescent. Freely and continuous basal branching with lateral branches potentially forming at every node.

*Usage.*—Appropriate for hanging baskets, window boxes and patio containers.

*Plant height (from soil level to top of plant plane).*—About 20 cm.

*Plant diameter.*—About 50 to 60 cm.

*Stem description.*—Main branches, length: About 80 cm. Main branches, diameter: About 4 to 6 mm. Lateral branches, length: About 32 to 48 cm. Lateral branches, diameter: About 2 mm. Internode length: About 3.2 cm. Texture: Densely pubescent. Color: 144A to 144B.

*Foliage description.*—Arrangement: Alternate; simple. Length: About 5.6 cm. Width: About 3.9 cm. Shape: Ovate to round. Apex: Obtuse. Base: Attenuate. Margin: Entire. Aspect: Flat. Texture, upper and lower surfaces: Leathery; pubescent. Venation pattern: Pinnate. Color: Developing foliage, upper and lower surfaces: 147B. Fully expanded foliage, upper surface: 147A to 147B. Fully expanded foliage, lower surface: 147B. Venation, upper surface: 147C. Venation, lower surface: 147B. Petiole length: About 8 to 12 mm. Petiole diameter: About 2.4 mm. Petiole color: 147B.

Flower description:

*Flower type and habit.*—Single salverform flowers; flowers face upward and outward; single, axillary. Freely flowering.

*Natural flowering season.*—Long day responsive; flowering from April until frost in the autumn in Germany; flowering continuous during this period.

*Fragrance.*—None detected.

*Flower longevity on the plant.*—About one week.

*Flower size.*—Diameter: About 7.4 cm. Depth (height): About 3.3 cm. Tube length: About 2.8 cm. Throat diameter, distal end: About 1.3 cm. Tube diameter, proximal end: About 5 mm.

*Flower buds.*—Length: About 3.3 cm. Diameter: About 6 mm. Shape: Oblong. Color: 138C to 144B overlain with N77C.

*Petals.*—Arrangement/appearance: Single whorls of five petals, fused into a flared trumpet. Length from throat: About 3.4 cm. Width: About 3.2 cm. Shape: Obtuse. Apex: Rounded. Margin: Entire. Texture, upper and lower surfaces: Smooth, satiny. Color: When opening, upper surface: 86A; towards the margins, 155D. When opening, lower surface: 83D overlain with N80B; towards the margins 155D. Fully opened, upper surface: N78A; towards the margins, 155D. Fully opened, lower surface: N81A to N81C; towards the margins, 155D. Flower throat (inside): N187A. Flower tube (outside): N77B overlain with N79B to N79C. Venation, upper surface: 79A. Venation, lower surface: N187A. Venation, throat: Similar to throat. Venation, tube: Similar to tube.

*Sepals.*—Arrangement/appearance: Single whorl of five sepals, fused at base; star-shaped. Length: About 2.2 cm. Width: About 7 mm. Shape: Ovate. Apex: Round, obtuse. Margin: Entire. Texture, upper and lower surfaces: Pubescent; leathery. Color, upper and surfaces: 144A.

*Peduncles.*—Length: About 3.6 cm. Width: About 2 mm. Strength: Wiry, strong. Texture: Pubescent. Color: 144A.

*Reproductive organs.*—Stamens: Quantity: About five per flower. Anther shape: Four-parted, reniform. Anther length: About 2.5 mm. Anther width: About 2.2 mm. Anther color: 195B overlain with 91B. Pollen amount: Moderate. Pollen color: 91C. Pistils: Quantity: One per flower. Pistil length: About 1.9 cm. Stigma shape: Ovate. Stigma color, immature: 137A. Stigma color, mature: 147A. Style length: About 1.4 cm. Style color: 144D. Ovary color: 144B. Seed/fruit: Seed and fruit production have not been observed.

Disease/pest resistance: Plants of the new *Petunia* have not been noted to be resistant to pathogens or pests common to *Petunia*.

Temperature tolerance: Plants of the new *Petunia* have been observed to be tolerant to temperatures from 2 to 30° C.

It is claimed:

1. A new and distinct cultivar of *Petunia* plant named 'Wespequeen', as illustrated and described.

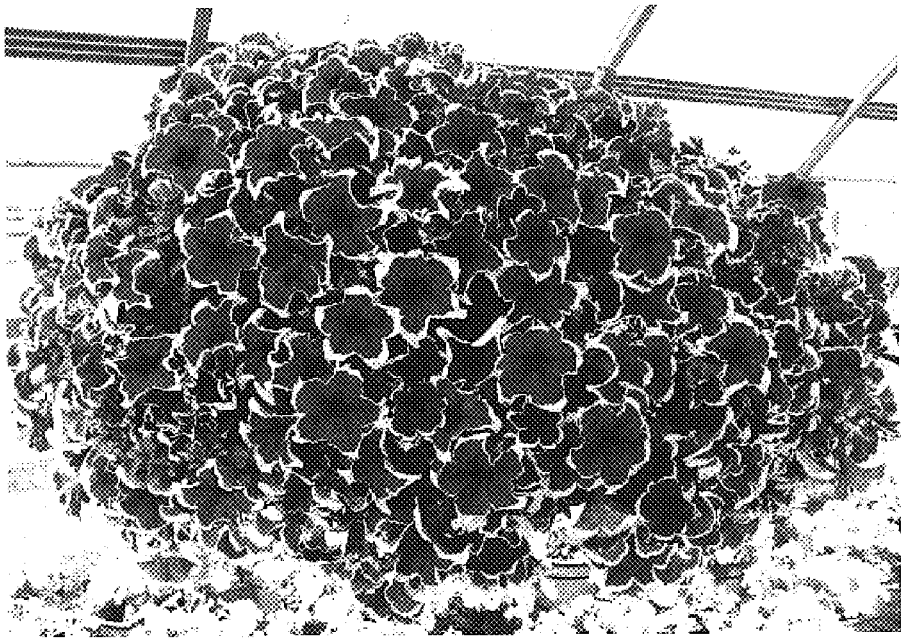

* * * * *